(12) United States Patent
Zhou et al.

(10) Patent No.: US 11,020,375 B2
(45) Date of Patent: Jun. 1, 2021

(54) EDARAVONE DOSAGE FORM

(71) Applicant: SUZHOU AUZONE BIOLOGICAL TECHNOLOGY CO., LTD, Suzhou (CN)

(72) Inventors: Xinfu Zhou, Fuijian (CN); Ankit Parikh, Fujian (CN); Sanjay Garg, Fujian (CN)

(73) Assignee: SUZHOU AUZONE BIOLOGICAL TECHNOLOGY CO., LTD., Sozhou (CN)

(*) Notice: Subject to any disclaimer, the term of this patent is extended or adjusted under 35 U.S.C. 154(b) by 0 days.

(21) Appl. No.: 16/084,668

(22) PCT Filed: Apr. 21, 2017

(86) PCT No.: PCT/CN2017/081405
§ 371 (c)(1),
(2) Date: Sep. 13, 2018

(87) PCT Pub. No.: WO2017/157350
PCT Pub. Date: Sep. 21, 2017

(65) Prior Publication Data
US 2019/0083463 A1 Mar. 21, 2019

(30) Foreign Application Priority Data
Mar. 16, 2016 (CN) .......................... 201610149832.9

(51) Int. Cl.
*A61K 31/4152* (2006.01)
*A61K 47/14* (2017.01)
*A61K 9/10* (2006.01)
*A61K 9/107* (2006.01)
*A61K 47/44* (2017.01)
*A61K 47/34* (2017.01)
*A61K 9/08* (2006.01)
*A61K 47/02* (2006.01)
*A61K 47/22* (2006.01)

(52) U.S. Cl.
CPC ............ *A61K 31/4152* (2013.01); *A61K 9/08* (2013.01); *A61K 9/10* (2013.01); *A61K 9/107* (2013.01); *A61K 47/02* (2013.01); *A61K 47/14* (2013.01); *A61K 47/22* (2013.01); *A61K 47/34* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 8,591,944 B2* | 11/2013 | Padval | B29C 48/04 424/465 |
| 8,658,684 B2* | 2/2014 | Yin | A61K 31/045 514/404 |
| 2008/0017202 A1 | 1/2008 | Michal et al. | |
| 2009/0131496 A1 | 5/2009 | Nabeta | |
| 2013/0259875 A1* | 10/2013 | Somera-Molina | A61K 38/35 424/173.1 |

FOREIGN PATENT DOCUMENTS

| | | |
|---|---|---|
| CN | 101536979 A | 9/2009 |
| CN | 101601656 A | 12/2009 |
| CN | 101933899 A | 1/2011 |
| CN | 101934037 A | 1/2011 |
| CN | 101966182 A | 2/2011 |
| CN | 102058531 A | 5/2011 |
| CN | 102526065 A | 7/2012 |
| CN | 103301119 A | 9/2013 |
| CN | 103536927 A | 1/2014 |
| CN | 104257603 A | 1/2015 |
| CN | 105816423 A | 8/2016 |
| EP | 2425814 A1 | 3/2012 |
| WO | 2009067343 A1 | 5/2009 |

OTHER PUBLICATIONS

Ito et al (Exp Neurol. Oct. 2008;213(2):448-55). (Year: 2008).*
PCT International Search Report and Written Opinion dated Jul. 19, 2017 from corresponding Application No. PCT/CN2017/081405, 11 pages.
Bernabeu et al., Colloids Surf B Biointerfaces, 2016. 140: p. 403-11.
Dian et al., Nanoscale Res Lett, 2014. 9(1): p. 2406.
Jin et al., Biomed Pharmacother, 2015. 69: p. 388-95.
Xia et al., Colloids Surf B Biointerfaces, 2016. 141: p. 301-310.
Strickley, Pharm Res, 2004. 21(2): p. 201-30.
Parikh, Ankit et al., Self-nanomicellizing solid dispersion of edaravone: part I—oral bioavailability improvement, Drug Design, Development and Therapy 2018:12, pp. 2051-2069.
Chinese medicine formulations of gastrointestinal transit and Design, Author: Ping Qi Neng, Publisher: Chemical Industry Press; Jul. 2010, pp. 78-81.
Xiang Jin et al, "Soluplus1 micelles as a potential drug delivery system for reversal of resistant tumor", Biomedicine & Pharmacotherapy 69 (2015) 388-395.
Jing Qin et al, "cRGD mediated liposomes enhanced antidepressant-like effects of edaravone in rats", European Journal of Pharmaceutical Sciences 58 (2014) 63-71.
Linghui Dian et al., "Enhancing oral bioavailability of quercetin using novel soluplus polymeric micelles", Nanoscale Research Letters 2014, 9:684, 11 pages.
Ye Xiaoqiang et al., "The properties of novel grafting polymer Soluplus@ and its application in pharmaceutics", Journal of Jilin Medical College Year 2015, Issue 5, p. 368-372.
Zeng Jian et al., "Preparation and Characterization of the Edaravone and Cyclodextrin Inclusion Complex", Chin JMAP, Sep. 2010, vol. 27 No. 9.
Office Action issued in Chinese Patent Application No. 201610149832. 9, dated Feb. 27, 2018, 7 pages.
Office Action issued in Chinese Patent Application No. 201810908492. 2, dated May 25, 2020, 7 pages.

(Continued)

*Primary Examiner* — Celeste A Roney
(74) *Attorney, Agent, or Firm* — Dilworth IP, LLC

(57) ABSTRACT

Disclosed is an Edaravone dosage form and a use thereof in preparing a drug used for treating diseases related to oxidative stress, the dosage form being selected from a lipid-based delivery system, a solid dispersion, micelles and a co-solvent based formulation.

9 Claims, 5 Drawing Sheets

(56) References Cited

OTHER PUBLICATIONS

Search Report Issued in Chinese Patent Application No. 2016101498329, dated Feb. 10, 2018, 3 pages.
Search Report Issued in Chinese Patent Application No. 2016101498329, dated Mar. 30, 2018, 2 pages.
Search Report Issued in Chinese Patent Application No. 2018109084922, dated May 19, 2020, 3 pages.
Search Report Issued in European Patent Application No. EP 17 76 5892, dated Dec. 17, 2019, 2 pages.
Written Opinion Issued in European Patent Application No. EP 17 765 892, dated Dec. 2019, 3 pages.
Search Report issued in Singapore Patent Application No. 11201808019W, dated Jan. 9, 2020, 2 pages.
Written Opinion issued in Singapore Patent Application No. 11201808019W, dated Jan. 10, 2020, 7 pages.
International Search Report issued in International Application No. PCT/CN2017/081405, dated Jul. 19, 2017, 4 pages.
Jhaveri, A. M. et al, Multifunctional polymeric micelles for delivery of drugs and siRN. Frontiers in Pharmacology, Apr. 25, 2014, vol. 5, No. 77, pp. 1-26.
Djuric, D., Chapter 5: Soluplus®. Solubility Enhancement with BASF Pharma Polymers Solubilizer Compendium, Oct. 30, 2011, pp. pp. 67-72.
Written Opinion issued in SG Patent Application No. 11201808019W dated Feb. 17, 2021.

* cited by examiner

EDARAVONE DOSAGE FORM

TECHNICAL FIELD

The present invention belongs to the pharmaceutical field. In particular, the present invention relates to a novel formulation of Edaravone, especially, an oral formulation, and use of Edaravone for treating oxidative stress related diseases of human effectively.

BACKGROUND ART

Free radicals are common outcome of normal aerobic cellular metabolism. In-built anti-oxidant system of human body plays its decisive role in prevention of any damage due to free radicals. However, imbalanced defense mechanism of anti-oxidants, overproduction or incorporation of free radicals from environment to living system results in serious impairment leading to a neuro-degeneration. Neural cells suffer functional or sensory loss in neurodegenerative diseases. Apart from several other environmental or genetic factors, oxidative stress (OS) results in free radical attacks on neural cells, making calamitous contribution to the neuro-degeneration. Although, oxygen is imperative for life, metabolic imbalance and excess reactive oxygen species (ROS) generation are the main causes of the global chronic and degenerative diseases like aging and other degenerative diseases such as human Alzheimer's disease (AD), Parkinson's disease (PD), Multiple Sclerosis (MS), amyolotrophic lateral sclerosis (ALS), atherosclerosis, cancer, diabetes, rheumatoid arthritis (RA), post-ischemic perfusion injury, myocardial infarction, cardiovascular diseases, chronic inflammation, stroke and septic shock. Based on the report from the World Health Organization (WHO), the top 10 deadliest diseases worldwide are ischemic heart disease, stroke, chronic obstructive pulmonary disease (COPD), lower respiratory infections, trachea/bronchus/lung cancers, HIV/AIDS, diarrhoeal diseases, diabetes mellitus, hypertension and tuberculosis (in descending order from top 1-10). In 2012, 28.8 million of patients in the word were dead from all these diseases (mostly due to the top 4 deadliest diseases); ischemic heart disease contributed approximately 25.7% to all the deaths, stroke contributed approximately 23.3% to all the deaths, while COPD and lower respiratory infections each contributed approximately 10.7% to all the deaths. According to a variety of researches, oxidative stress is the main cause associated with most of these top 10 deadliest diseases especially ischemic heart disease, stroke, COPD, HIV/AIDS and diabetes mellitus. The global market associated with oxidative stress related disease is above 200 billion USD.

Since oxidative stress is the root of many chronic, degenerative and deadliest diseases, this suggests the dire need of anti-oxidant agents in helping to control body ROS level tightly. Therefore, as a strong and potent free radical scavenger or anti-oxidant, Edaravone can play an important role in lowering the ROS level and reducing oxidative stress. Thus, it is expected that Edaravone may potentially treat or minimize the risk of such deadly diseases in the near future.

Edaravone, also known as MCI-186, has a chemical name: 3-methyl-1-phenyl-2-pyrazol-5-one, a molecular formula of $C_{10}H_{10}N_2O$, a molecular weight of 174.19, and a structure as shown below:

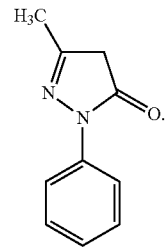

It is a strong and synthetic free oxygen radical scavenger that has anti-oxidant action to reduce oxidative stress and inhibit lipid peroxidation via both nonenzymatic lipid peroxidation and the lipoxygenase pathways. But besides these effects, Edaravone also exhibits beneficial actions in inflammation, matrix metalloproteinases, nitric oxide production and apoptotic cell death. Mitsubishi Tanabe Pharma Corporation (Osaka, Japan) developed Edaravone and introduced as Radicut in 2001 to be the first neurovascular protective drug in the world. It was approved by Japanese Ministry of Health and Welfare (JMHW) in 2001 for the treatment of patients who suffered from cerebral infarction, and acute ischemic stroke (AIS). Since then, Edaravone has not only been used commonly to treat AIS, but also been used to treat other ROS-related diseases such as cardiovascular diseases and stoke. Although Edaravone is very common and extensively prescribed in Japan, India and China for various treatment, it has not been approved by FDA in US or other western countries. This is due to its toxic effects in liver as well as kidney and the lack of clinical studies that support the beneficial effects of Edaravone. However, there are many countries currently conducting clinical investigation on Edaravone.

Edaravone is designed to be a phenol-like compound; phenol is one of the functional groups in all the phenolic anti-oxidant, which consists of a hydroxyl (—OH) group attached to an aromatic ring and is responsible for its anti-oxidant property. Phenols quench free radicals by donating one hydrogen ion to the free radical and in turn becoming a radical; however, the electrons in the phenol are stabilized by the aromatic ring via resonance electron delocalization and become less active. But due to the toxic and corrosive properties of phenols, they are not applicable for pharmaceutical use even though they have exhibited radical scavenger action and have proven to be potent anti-oxidants.

On the other hand, Edaravone is expected to have the same activities as phenols and show similar anti-oxidant and free radical scavenging effects due to its aromatic hydroxyl group. Edaravone can be categorized into three different tautomeric forms; the amine form, keto form, and enol form, and the aromatic hydroxyl group is produced via keto-enol tautomerization. However, in contrary to phenols, Edaravone do not have the toxicity effects and this is one of the reasons why Edaravone is preferred over phenols.

Edaravone has a pKa value of 7.0, hence roughly 50% of Edaravone molecules are ionized and exist in anionic forms at physiological pH. The anionic form of Edaravone is also the more reactive form which may readily react with ROS in the brain to bring about the anti-oxidant effects. The advantages Edaravone has over other free radical scavengers such as Idebenone, Baicalein and catechins (flavocoxid) are that blood brain barrier permeation is not a major hurdle as Edaravone is a lipophilic molecule with low molecular weight and has solubility property in both water and lipid. Therefore, it can readily cross the blood brain barrier to act at the target site in the brain. The relative ratio of plasma to cerebral spinal fluid levels of Edaravone is estimated to be between 50 and 65%. These properties may be the reason of the neuroprotective actions of Edaravone in cerebral infarction when other anti-oxidants do not exhibit such an effect.

Currently, the only available marketed formulation of Edaravone is parenteral delivery formulation, e.g., injection. However, it is not suitable for long-term therapy on patient compliance view. Therefore, another dosage, especially, an oral formulation is a dire need for Edaravone to achieve best therapeutic output. However, preliminary data generated by the present inventors and others show that poor water solubility, poor permeation, poor bioavailability, poor aqueous stability, short half-life, and some adverse effects like hepatotoxicity and nephrotoxicity of Edaravone can make a major hurdle in achieving an expected therapeutic output in preclinical and clinical studies for any oxidative stress related diseases.

Studies of oral administration of Edaravone may refer to the Chinese Patent Application No. CN101953832A, which discloses an oral pharmaceutical composition of Edaravone with inclusion of β-cyclodextrin and its preparation method, comprising 1 part of Edaravone and 6-100 parts of cyclodextrin by mass based on the composition. Needs still exist for another formulation with better effects in the art.

SUMMARY OF INVENTION

To achieve a viable novel oral formulation, this application has used co-solvent based, solid dispersion and lipid based formulation strategy which can address all of the issues mentioned above and results in a best therapeutic output.

1) lipid-based drug delivery system: lipid-based drug delivery systems have shown great potentials in oral delivery of pharmaceutically difficult candidates, with several successfully marketed products. Pre-dissolving drugs in lipids, surfactants, or mixtures of lipids and surfactants omits the dissolving/dissolution step, which is a potential rate limiting factor for oral adsorption of poorly water-soluble drugs so as to improve bioavailability, bypasses the liver in order to reduce hepatotoxicity due to absorption from lymphatic route and also reduces the nephrotoxicity due to undiscovered mechanism. The lipid-based drug delivery system includes a lipid solution, a lipid suspension, a self-emulsifying drug delivery system, surfactant or polymer-lipid mixed micelles, and a nano-emulsion formulation.

2) solid dispersion based strategy: solid dispersion technology is the science of dispersing one or more active ingredients in an inert matrix in the solid stage in order to achieve improved bioavailability by increasing solubility, dissolution rate and permeation, sustained release of drugs, altered solid state properties, and increased stability.

3) co-solvent based strategy: some poorly water-soluble molecules are sufficiently solubilized in solutions composed of an aqueous/organic co-solvent whereas other poorly water-soluble molecules are solubilized only in solutions that are entirely organic or composed of either one solvent or a mixture of solvents/surfactants. This strategy is most widely used for oral administration of pharmaceutically difficult candidates to achieve improved bioavailability.

The primary objective of the present invention is to make efficient use of Edaravone in order to receive the best therapeutic output by achieving desired bioavailability, extended half-life, and reduced adverse effects related to liver and kidney. The solid, semi-solid and liquid formulations of Edaravone are co-solvent based system, lipid solutions, lipid suspension, self-emulsifying drug delivery systems, micellar[1-4], nano-emulsion, and solid dispersion. The present invention represents a robust approach for Edaravone to be supplied in form of solid dosage form like tablet or powder fill in hard gelatin capsule or liquid dosage form like liquid-fill hard capsules or soft gelatin capsules.

Specifically, the present invention relates to Edaravone formulation 1 (lipid formulation) and its preparation method, as follows:

The present invention provides a lipid-based drug delivery system comprising Edaravone or its pharmaceutically acceptable salt thereof as an active ingredient, and a lipid.

According to the present invention, lipid refers to a natural or artificial synthetic fat comprising triglyceride and saturated or unsaturated fatty acids with different lengths of carbon chains, preferably Caproyl 90, Capmul MCM and Caproyl™ PGMC.

According to the present invention, lipids include natural product oil, semi-synthetic lipids (prepared by chemically combining medium-chain saturated fatty acids or glycerides derived from natural product plant oil, with one or more hydrophilic chemical entities) and fully-synthetic lipids (mainly natural glycolic acid). Water-insoluble lipids include bee wax, oleic acid, soy fatty acid, d-α-Tocopherol (vitamin E), corn oil mono-di-triglyceride, medium chain (C8/C10) mono and diglyceride, and propylene glycol ester of fatty acid.

Lipid may be triglycerides, and further divided into long chain triglyceride (LCT), medium chain triglyceride (MCT) and short chain triglyceride (SCT). Wherein, LCT includes hydrogenated soybean oil, hydrogenated vegetable oil, corn oil, olive oil, soybean oil, peanut oil, and sesame oil, and MCT includes caprylic/capric triglyceride derived from coconut oil or palm seed oil. Specifically, in the lipid-based drug delivery system, corn oil, cotton seed oil, Captex 355, peceol, peanut oil, caprylic triglyceride, castor oil, sesame oil, Miglyol 812, sunflower oil, Capmul MCM, and Caproyl PGMC may be used as the lipid.

According to the present invention, the lipid-based drug delivery system includes a therapeutic agent (Edaravone), an oily media/lipid, a surfactant, a co-surfactant, a cosolvent, a liposome and/or solid lipid nanoparticles, and the like.

According to the present invention, the lipid-based drug delivery system further includes excipients and/or additives. Wherein, the excipients are chemically triglycerides, partially triglycerides, semi-synthetic oily esters and semi-synthetic non-ionic surfactant esters, or are selected from water-insoluble bee wax, oleic acid, soy fatty acid, d-α-Tocopherol (vitamin E), corn oil mono-di-triglyceride, medium chain (C8/C10) mono and diglyceride, and propylene glycol ester of fatty acid.

The additive includes a solid absorbent, a water-soluble and lipid-soluble anti-oxidant, an acidifying agent, a chelating agent and a buffering agent, wherein the solid absorbent includes a silica based absorbent and a non-silica based absorbent. The silica based absorbent includes Aerosil 200 and magnesium alumina meta silicate, and the non-silica based absorbent includes microcrystalline cellulose, talc, dicalcium phosphate anhydrous (DCPA), and the water-soluble polymer consisting of alkylcellulose, hydroxyalkylcellulose, hydroxyalkylalkylcellulose sugar. The chelating agent is selected from at least one of ethylenediamine, calcium disodium edetate and disodium edetate. The acidifying agent includes but is not limited to citric acid, acetic acid, fumaric acid, hydrochloric acid and nitric acid. The buffering agent includes but is not limited to potassium metaphosphate, potassium dihydrogen phosphate, sodium acetate and sodium citrate. The water-soluble or lipid-soluble anti-oxidant includes but is not limited to ascorbic acid, ascorbyl palmitate, butyl hydroxy anisole, butylated hydroxy toluene, hypophosphorous acid, monothioglycerol, propyl gallate, sodium ascorbate, sodium bisulfite, sodium formaldehyde sulfoxylate, sulfoxylate and sodium metabisulfite.

According to the present invention, the lipid-based drug delivery system further comprises Capryol™ PGMC, Cremophor® RH 40, Labrasol, TPGS 1000, Transcutol P and/or Aerosil 200, in addition to Edaravone.

According to the present invention, the lipid-based drug delivery system further comprises a water-soluble organic solvent, a surfactant, a co-surfactant, a polymer solubilizer, a phospholipid, an acidulant, a buffering agent, a stabilizer, an anti-oxidant, a preservative, and/or a solid adsorbent. The water-soluble organic solvent includes but is not limited to PEG 200-10,000, polyvinyl caprolactam (PCL), polyvinyl acetate (PVA) or a copolymer thereof, a water-soluble form of vitamin E and ethanol, wherein PEG200-10,000 includes, for example, PEG 300, PEG 400, PEG 1,000 and PEG 6,000, used as both a water-soluble organic solvent and a solubilizer. The surfactants include water-soluble surfactants and water-insoluble surfactants. The water-soluble surfactants refer to a derivative of dietary oil where fatty acid components can be either unsaturated or saturated, synthesized by a reaction of polyethylene glycol (PEG) with hydrolysed vegetable oils, a reaction of an alcohol with ethylene oxide to produce alkyl ether ethoxylates, or a reaction of polysorbates-based vegetable oils with ethylene oxide, including but not limited to Cremophor RH 40, Labrasol, TPGS 1000, Tween 20, Cremophor E1 and Tween 80. The co-surfactant is based on polyethylene glycol, polypropylene glycol, glycerol and ethanol, especially it is selected from PEG 300, PEG 400, propylene glycol, glycerol, ethanol, Transcutol HP and Transcutol P. The polymer solubilizer includes but is not limited to Soluplus, Chitosan, poly(vinyl pyrrolidone) (PVP), PVP/VA, HPC, HPMC, HPMCAS, eudragit E100, and a cationic copolymer based on dimethylaminoethyl methacrylate, butyl methacrylate, and methyl methacrylate, as both a polymer solubilizer and a stabilizer.

According to the present invention, the lipid-based drug delivery system further comprises a polymer carrier selected from Soluplus, hydroxypropyl methyl cellulose (HPMC), polyethylene glycol (PEG), Chitosan, PVP, PVP/VA, HPC, hydroxypropylmethylcellulose acetate (HPMCAS), eudragit E100, and a cationic copolymer based on dimethylaminoethyl methacrylate, butyl methacrylate, and methyl methacrylate, preferably Soluplus, HPMC or PEG.

According to the present invention, the lipid-based drug delivery system is selected from a lipid solution, a lipid suspension, surfactant or polymer-lipid mixed micelles, a self-microemulsifying drug delivery system (SMEDDS), and a nanoemulsion formulation.

According to the present invention, in the lipid-based drug delivery system, SMEDDS is solid, and it further comprises a solid absorbent, preferably Aerosil 200.

According to the present invention, in the lipid-based drug delivery system, the nanoemulsion formulation further comprises a water/buffering agent.

The present invention further provides a method of preparing the lipid-based drug delivery system, comprising a step of:

Dissolving Edaravone or its pharmaceutically acceptable salt thereof as an active ingredient into a lipid, a surfactant, or a mixture of the lipid and the surfactant.

The present invention also relates to Edaravone formulation 2 (solid phase dispersion) and its preparation method, as follows:

The present invention provides a solid phase dispersion formulation, comprising Edaravone or its pharmaceutically acceptable salt thereof as an active ingredient, and a polymer carrier.

According to the present invention, the polymer carrier is a water-soluble polymer selected from the group consisting of homopolymer of N-vinyllactam, copolymer of N-vinyllactam, cellulose ester, cellulose ether, polyalkylene oxide, polyacrylate, polymethacrylate, homo- and co-polymers of acrylic acids, homo- and co-polymers of methacrylic acids, polyacrylamide, polyvinyl alcohol, vinyl acetate polymer, copolymers of vinylacetate, carboxyvinyl polymer, oligosaccharide, polysaccharide and mixtures thereof.

According to the present invention, the water-soluble polymer is selected from the group consisting of alkylcellulose, hydroxyalkylcellulose, hydroxyalkylalkylcellulose, methylcellulose (MC), ethylcellulose (EC), hydroxyethylcellulose (HEC), hydroxypropyl cellulose (HPC), hydroxypropylmethylcellulose (HPMC), hydroxyethylmethylcellulose(HEMC), hydroxypropylmethylcellulose succinate, hydroxypropylmethyl cellulose acetate succinate, carboxymethylethylcellulose, sodium carboxymethylcellulose, pottasium carboxymethyl cellulose, cellulose acetate succinate, cellulose acetate phthalate, hydroxypropylmethylcellulose phthalate, polyacrylic acid copolymer, poly(meth) acrylic acid polymers, poly(hydroxyalkyl acrylates), poly (hydroxyalkyl methacrylates), polyvinylpyrrolidone (PVP), homopolymers of vinylpyrrolidone, copolymers of vinylpyrrolidone, povidone, vinylpyrrolidone-vinylacetate copolymer (copovidone), copolymers of vinyl acetate, copolymers of vinyl propionate, copolymers of vinyl acetate and crotonic acid, polyethylene glycol, polyvinyl alcohol, partially hydrolyzed polyvinyl acetate, gelatin, sodium alginate, soluble starch, gum acacia, dextrin, hyaluronic acid, sodium chondroitin sulfate, propylene glycol alginate, agar, tragacanth, xanthan gum, aminoalkyl methacrylate copolymers, polyvinyl-acetal-diethylaminoacetate, methacrylate copolymer, methacrylic acid copolymer L, methacrylic acid copolymer LD, methacrylic acid copolymer S, macrogol, polyethylene oxide, polypropylene oxide, copolymers of ethylene oxide (EO) and propylene oxide (PO), carrageenans, galactomannans and mixtures thereof.

According to the present invention, the polymer carrier is selected from Soluplus, hydroxypropyl methyl cellulose (HPMC), polyethylene glycol (PEG), Chitosan, PVP, PVP/VA, HPC, hydroxypropylmethylcellulose acetate (HPMCAS), eudragit E100, and a cationic copolymer based on dimethylaminoethyl methacrylate, butyl methacrylate and methyl methacrylate, preferably from Soluplus, HPMC or PEG.

According to the present invention, the solid phase dispersion formulation further comprises a surfactant (anionic, cationic or amphoteric surfactant) selected from the group consisting of sodium dodecanesulfonate, sodium dodecyl sulfate (SDS), sodium lauryl sulfate (SLS), polyoxyethylene sorbitan long-chain fatty acid esters, Vitamin E-TPGS, bile salts, sodium deoxycholate, sodium glycocholate, polyoxyethylene polyoxypropylene glycols and combinations thereof. Preferably, the surfactant is TPGS 1000.

According to the present invention, the solid phase dispersion formulation comprises Edaravone, Soluplus and optionally TPGS 1000.

According to the present invention, the solid phase dispersion formulation further comprises pharmaceutically acceptable excipients selected from the group consisting of a disintegrant, a lubricant, a glidant, an anti-adherent, an inert filler, a wetting agent, a pH modifier, a binder, a solubility modifier, a recrystallization inhibitor, a diluent and combination thereof.

According to the present invention, the solid phase dispersion formulation may be formulated into a tablet, a ring, a patch, a capsule, a pellet, granules, fine granules or powders.

The present invention further provides a method of preparing the solid phase dispersion formulation, comprising a step of:

Dispersing Edaravone or a pharmaceutically acceptable salt thereof as an active ingredient in a polymer carrier and, optionally, a surfactant, preferably prepared by a step selected from: melting ice bath agitation, thin film cooling, liquid nitrogen, spray congealing, hot-melt extrusion, Meltrex™, melt agglomeration or solvent evaporation (oven drying, vacuum drying, rotary evaporation, heating on hot plate, spray drying, freeze drying, supercritical anti-solvent, co-precipitation, electrostatic spinning, spray freeze drying, ultra-rapid freezing, fluid-bed coating) and melting solvent.

The present invention also relates to Edaravone formulation 3 (a micelle-based formulation) and its preparation method as follows:

The present invention provides a micelle-based formulation, comprising Edaravone or its pharmaceutically acceptable salt thereof as an active ingredient, a polymer carrier and water/a buffering agent. An effective amount of Edaravone is included in the micelle.

According to the present invention, the polymer carrier is selected from Soluplus, hydroxypropyl methyl cellulose (HPMC), polyethylene glycol (PEG), Chitosan, PVP, PVP/VA, HPC, hydroxypropylmethylcellulose acetate (HPMCAS), eudragit E100, a cationic copolymer based on dimethylaminoethyl methacrylate, butyl methacrylate, and methyl methacrylate, preferably from Soluplus, HPMC or PEG.

According to the present invention, the micelle-based formulation further comprises a surfactant, a solid phase adsorbent, an acidifying agent and/or an anti-oxidant.

According to the present invention, the micelle-based formulation comprises Edaravone, Soluplus, TPGS 1000 and PBS.

The present invention further provides a method of preparing the micelle-based formulation, comprising steps of:

Dissolving Edaravone or its pharmaceutically acceptable salt thereof as an active ingredient, a polymer carrier and optionally a surfactant, in ethanol, Removing the organic solvent by rotary evaporation, Drying in vacuo after formation of a film, then adding a buffer for hydration, and Sonicating.

The present invention also provides a method of protecting Edaravone as a therapeutic agent, comprising entrapping the therapeutic agent within the micelle-based formulation.

The present invention also relates to Edaravone formulation 4 (a co-solvent-based formulation) and its preparation method as follows:

The present invention provides a co-solvent-based formulation, comprising Edaravone or its pharmaceutically acceptable salt thereof as an active ingredient, and 1-99% (v/v) of a water-soluble organic solvent and/or a surfactant or co-surfactant.

According to the present invention, the water-soluble organic solvent includes but is not limited to PEG 200-10,000, propane diol, glycerol, Transcutol HP, Transcutol P, Cremophor RH 40, Cremophor EL, Labrasol, TPGS 1000, Tween 20, Tween 80, a water-soluble form of vitamin E, and ethanol, wherein PEG 200-10,000 includes, e.g., PEG 300, PEG 400, PEG 1,000 and PEG 6,000.

According to the present invention, the co-solvent-based formulation further comprises a surfactant, a phospholipid, vitamin E, an anti-oxidant, a preservative, a solid phase adsorbent and/or water/a buffer, for solubilization and for improvement of permeability and stability.

According to the present invention, the co-solvent-based formulation further comprises one or more of PEG 300, Labrasol, Transcutol P, TPGS 1000 and Cremophor RH 40, in addition to Edaravone as an active ingredient.

The present invention also provides a method of preparing the co-solvent-based formulation, comprising a step of:

Dissolving Edaravone or its pharmaceutically acceptable salt thereof as an active ingredient in a water-soluble organic solvent and/or a surfactant.

The present invention also relates to a dosage form of the Edaravone formulation and an administration route as follows:

The above Edaravone formulations 1-3 may be formulated as a solid dosage form, selected from a tablet, a capsule, powders or strips (strip), by oral, parenteral, inhalation, topical or transdermal, intranasal, ocular, ear, rectal, vaginal route.

The above Edaravone formulations 1-4 may be formulated as a liquid dosage form, selected from a solution, a suspension, an emulsion, a co-solvent-based system, an aerosol, by oral, parenteral, inhalation, topical or transdermal, intranasal, intraocular, ear, rectal, vaginal route.

The above Edaravone formulations 1-4 may be formulated as a semi-solid dosage form, selected from an ointment, a cream, a gel, a paste, by topical or transdermal route, for a topical or systemic administration purpose.

The present invention also relates to a method for treating a disease using the Edaravone formulation and its pharmaceutical use as follows:

The present invention provides use of Edaravone formulations 1-4 for treatments of an oxidative stress related disease.

The present invention provides use of Edaravone formulations 1-4 in preparation of a medicament for treatment of an oxidative stress related disease.

According to the present invention, the oxidative stress-related disease includes aging diseases (arthritis, diabetes, osteoarthritis, cataract, macular degeneration, prostate problems), cardio-vascular diseases (arteriosclerosis, heart failure, heart attack, kidney failure, high blood pressure, stroke, impaired circulation, cholesterol and plaque formation, reperfusion injury), cancers (prostate cancer, breast cancer, lung cancer, colorectal cancer, bladder cancer, uterine cancer, ovarian cancer, lymphoma, skin cancer, stomach cancer, liver cancer and other wasting diseases), neurodegenerative diseases (Parkinson disease, Alzheimer disease, multiple sclerosis, schizophrenia, dementia, Huntington's disease), liver diseases (toxic hepatitis, viral hepatitis (A, B, C), chronic hepatitis), lung diseases (asthma emphysema, Pneumonia, Bronchitis (chronic and acute), cystic fibrosis, pulmonary fibrosis, chronic obstructive pulmonary disease (COPD), adult respiratory distress syndrome (ARDS)), digestive diseases (inflammatory bowel disease, ulcerative colitis, Cohn's disease, gastritis, stomach cancer, peptic ulcer, pancreatitis), renal failure and dialysis (kidney failure, renal toxicity, oxidative stress from dialysis), infectious diseases and immunological diseases (viral infection HIV and AIDS, toxic hepatitis & cirrhosis, viral hepatitis (A, B, C), herpes, common cold, bacterial infection, chronic fatigue syndrome, certain autoimmune dysfunction), skin disorders (psoriases, eczema, SLE (lupus), vasculitis, polymyositis, mycosis fungoides, scleroderma, pemhigoid, atopic dermatitis, contact dermatitis, sebborrheic, dermatitis, dermatitis herpetiformis, acne conglobate, acne vularis, UV radiation skin damage), Eye, Ear, Nose, Throat & Teeth diseases (cataract, glaucoma, macular degeneration, hearing loss, ear infection, sinusitis, periodontal (gum) disease, Nose, mouth & throat (upper respiratory tract) disease), pregnancy, lactation and childbirth related diseases (pre-eclampsia, eclampsia, hypertension, diabetes), exercise & athletic diseases (over-training syndrome & the related oxidative stress), male problems (prostate enlargement, prostate cancer, balding and hair loss, male infertility), female infertility, joint disorders, or chronic inflammation, especially Alzheimer's disease, ALS, Parkinson's disease, ischemic heart disease, cerebral infarction/stroke, COPD, HIV/AIDS and diabetes.

Edaravone formulation or any components, either in individual or in combination, intends to modify/improve Edaravone's existing profile like solubility, chemical stability (hydrolysis, oxidation, thermal, light), sustained release, and pharmacokinetic properties like permeability through small intestine, bioavailability, half-life, metabolism, elimination and so on.

Among all the Edaravone formulations of the present invention, content of Edaravone is 0.001-1000 mg/ml, preferably 0.1-100 mg/ml, more preferably 10-20 mg/ml in a liquid formulation, and dose of Edaravone is 0.001-1000 mg/unit, preferably 0.1-100 mg/unit, more preferably 10-20 mg/unit in a solid formulation.

The present invention provides a novel Edaravone formulation using a strategy of solid phase dispersion, to greatly improve its solubility, stability and bioavailability. For example, by means of Soluplus, the present invention increases the solubility by 16 folds and has a comparable bioavailability relative to an i.v. formulation known in the art.

DESCRIPTION OF THE FIGURES

To clearly indicate the technical solution of the present invention, a brief introduction thereto is provided below in reference to the Figures. Apparently, these Figures are merely some embodiments recorded in this application. The present invention includes but is not limited to these Figures.

EMBODIMENTS

Figure 1:
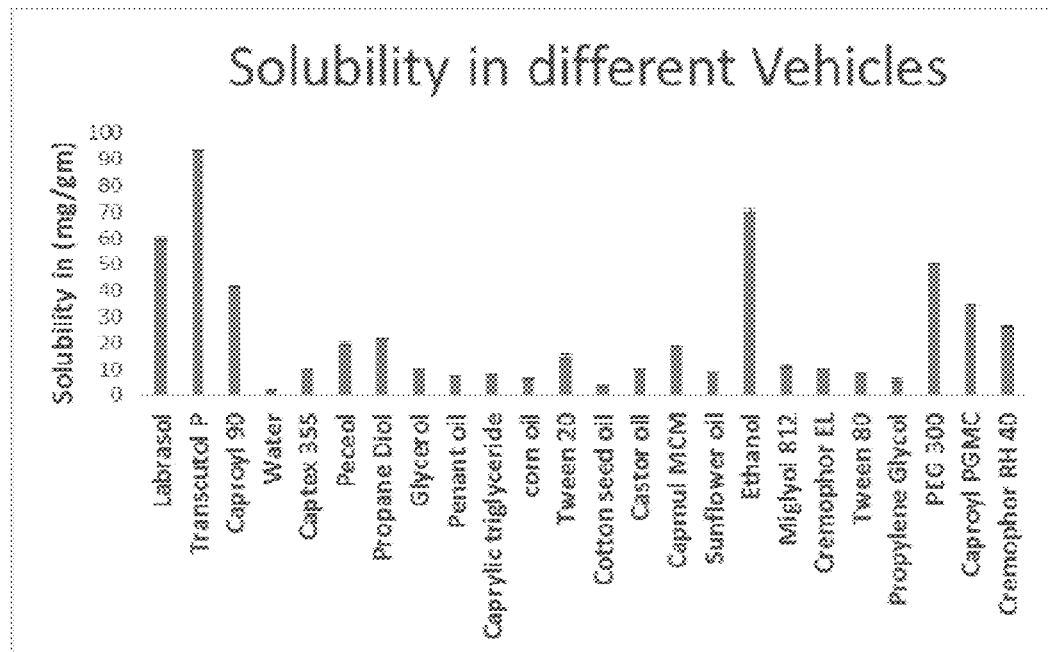
FIG. 1 shows the solubility of Edaravone (mg/gm) in various vehicles.

To further understand the present invention, preferable solutions of the present invention are described in details below in reference to examples.

However, these examples are merely used to illustrate the characteristics and merits of the novel Edaravone formulations of the present invention, but not to limit the protection scope of the present invention.

Components used in the invention with their chemical names[5]:

| Components | Use | Chemical names and other names |
|---|---|---|
| Capryol ™ PGMC | Oil | Propylene glycol monocaprylate (type I) NF |
| Cremophor ® RH 40 | Surfactant | Kolliphor ® RH 40, Macrogolglycerol hydroxystearate, PEG-40 castor oil, Polyoxyl 40 hydrogenated castor oil |
| Labrasol | Surfactant | Caprylocaproyl polyoxylglycerides, Caprylocaproyl macrogol-8 glycerides EP, Caprylocaproyl polyoxyl-8 glycerides NF |
| TPGS 1000 | Surfactant | D-α-Tocopherol polyethylene glycol 1000 succinate, Vitamin E polyethylene glycol succinate, Vitamin E-TPGS, Water soluble form of Vitamin E |
| Transcutol P | Co-surfactant | Transcutol HP, highly purified diethylene glycol monoethyl ether EP/NP |
| Aerosil 200 | Solid adsorbent | Fumed silicon dioxide (fumed silica) |
| Soluplus | Polymer solubilizer and stabilizer | Polyvinyl caprolactam-polyvinyl acetate-polyethylene glycol graft copolymer (PCL-PVAc-PEG) |
| PEG 300 | Water-soluble organic solvent, solubilizer | Polyethylene glycol 300 (300 is molecular weight) |
| If desired, all aqueous buffer systems may be used to prepare liquid formulation of Edaravone | | |
| Acidifying agents | | Citric acid, acetic acid, fumaric acid, hydrochloric acid, nitric acid |
| Anti-oxidants | | Ascorbic acid, ascorbyl palmitate, butylated hydroxyanisole, butylated hydroxytoluene, hypophosphorous acid, monothioglycerol, propylgallate, sodium ascorbate, sodium bisulfate, sodium formaldehyde sulfoxylate, sulfoxylate, sodium metabisulfite |
| Buffering agents | | Potassium metaphosphate, potassium phosphate, monobasic, sodium acetate, sodium citrate, anhydrous and dihydrate |

Example 1

Lipid Based Self-Emulsifying Drug Delivery System (SMEDDS) Formulation

| Ingredients | Quantity |
|---|---|
| Edaravone | 10 mg/ml |
| Capryol ™ PGMC | 30% |
| Cremophor RH 40 | 23.33% |
| Labrasol:TPGS 1000 (4:1) | 23.33% |
| Transcutol P | 23.33% |

Example 2

Lipid Based SMEDDS Formulation

| Ingredients | Quantity |
| --- | --- |
| Edaravone | 10 mg/ml |
| Capryol ™ PGMC | 30% |
| Cremophor RH 40 | 23.33% |
| Labrasol:TPGS 1000 (4:1) | 23.33% |
| Transcutol P | 23.33% |
| Aerosil 200 (Adsorbent) | 5% w/v |

Example 3

Lipid Based SMEDDS Formulation

| Ingredients | Quantity |
| --- | --- |
| Edaravone | 10 mg/ml |
| Capryol ™ PGMC | 30% |
| Cremophor RH 40 | 23.33% |
| Labrasol | 23.33% |
| Transcutol P | 23.33% |

Example 4

Lipid Based SMEDDS Formulation

| Ingredients | Quantity |
| --- | --- |
| Edaravone | 10 mg/ml |
| Capryol ™ PGMC | 30% |
| Labrasol | 46.66% |
| Transcutol P | 23.33% |
| Aerosil 200 (Adsorbent) | 5% w/v |

Example 5

Lipid Based Nanoemulsion Formulation

| Ingredients | Quantity |
| --- | --- |
| Edaravone | 10 mg/ml |
| Capryol ™ PGMC | 30% |
| Cremophor RH 40 | 23.33% |
| Labrasol:TPGS 1000 (4:1) | 23.33% |
| Transcutol P | 23.33% |
| Water | Q.S. |

Example 6

Micellar Formulation

| Ingredients | Quantity (mg) |
| --- | --- |
| Edavarone | 100 |
| Soluplus:TPGS 1000 | 500:200 |
| PBS (pH 7.4) | 10 ml |

Example 7

Solid Dispersion Formulation

| Ingredients | Quantity (mg) |
| --- | --- |
| Edavarone | 100 |
| Soluplus:TPGS 1000 | 500:75 |

Example 8

Solid Dispersion Formulation

| Ingredients | Quantity (mg) |
| --- | --- |
| Edaravone | 100 |
| Soluplus | 500 |

Example 9

Co-Solvent-Based Formulation

| Ingredients | Quantity |
| --- | --- |
| Edaravone | 20 mg/ml |
| Cremophor RH 40 | 250 mg |
| PEG 300 | 250 mg |
| TPGS 1000 | 125 mg |
| Water | 375 mg |

Example 10

Co-Solvent-Based Formulation

| Ingredients | Quantity |
| --- | --- |
| Edaravone | 20 mg/ml |
| Labrasol | 500 mg |
| TPGS 1000 | 125 mg |
| Water | 375 mg |

Example 11

Co-Solvent-Based Formulation

| Ingredients | Quantity |
| --- | --- |
| Edaravone | 20 mg/ml |
| PEG 300 | 500 mg |
| TPGS 1000 | 125 mg |
| Water | 375 mg |

Preparation Example 1

Preparation of Liquid Self-Micro Emulsified Drug Delivery Systems (SMEDDS, Examples 1 and 3)

Referring to Examples 1 and 3, the required amounts of Oil (Capmul PGMC), surfactants (Cremophor RH 40, Labrasol and TPGS 1000) and Co-surfactant (Transcutol P) were accurately weighed into glass vials. Then, the components were mixed by gentle stirring and vortex mixing, and heated at 37° C. in an incubator. The required amount of Edaravone was added and vortex mixing was performed, until Edaravone has perfectly dissolved.

Preparation Example 2

Preparation of Solid Self-Micro Emulsified Drug Delivery Systems (Examples 2 and 4)

Liquid SMEDDS formulation was prepared as mentioned above. It was diluted in the minimum quantity of miliQ water and stirred at room temperature for 2 h after adding a required quantity of Aerosil 200. The resultant mixture was then allowed to stand for 15 min to attain the equilibrium and filtered through 0.45 µm syringe filter (PVDF). Before Freeze Drying, solutions were frozen at −80° C. for at least 6 h and then subjected to lyophilization in Novalyphe-NL 500 (Savant Instruments Corp., Holbrook, N.Y.) for at least 24 h at −45° C. and 7102 mbar pressure. The solid SMEDDS were then stored in a desiccator.

Preparation Example 3

Preparation of Nano-Emulsion Based System (Example 5)

Referring to Example 5, the required amounts of Oil (Capmul PGMC), surfactants (Cremophor RH 40, Labrasol and TPGS 1000) and Co-surfactant (Transcutol P) were accurately weighed into glass vials. Then, the components were mixed by gentle stirring and vortex mixing, and heated at 37° C. in an incubator. The required amount of Edaravone was added and vortex mixing was performed, until Edaravone has perfectly dissolved. The required quantity of miliQ water was added dropwise until a clear formulation was obtained.

Preparation Example 4

Preparation of Micellar Formulation (Example 6)

Referring to Example 6, a required quantity of Edaravone, Soluplus and TPGS 1000 was dissolved in Ethanol. The organic solvent was removed by Buchi Rotavap II instrument. The film formed was dried in vacuum desiccator overnight, and then hydrated with 10 mL 1× PBS buffer (pH 7.4), incubated at 37° C. for 30 min, and then sonicated for a few minutes. The resultant mixture was filtered through 0.45 µm syringe filter (PVDF).

Preparation Example 5

Preparation of Solid Dispersion Based Formulations (Examples 7 and 8)

Referring to Examples 7 and 8, a required quantity of Edaravone, Soluplus with and without TPGS 1000 was dissolved in ethanol. The organic solvent was removed by Buchi Rotavap II instrument. The film formed was dried in a vacuum desiccator overnight. Dried samples were scrapped off from the flask and collected in a mortar. Powders were crushed and made homogenous by using mortar pestle.

Preparation Example 6

Preparation of Co-Solvent Based Formulations (Examples 9, 10 and 11)

Referring to Examples 9-11, all components were accurately weighed into glass vials. Then, the components were mixed by gentle stirring and vortex mixing, and heated at 37° C. in an incubator. The required amount of Edaravone was added and vortex mixing was performed, until Edaravone has perfectly dissolved.

Examples 1-11 provide a number of formulations, including lipid, micelles, solid dispersion and co-solvent based formulations. Advantages of these formulations are shown by effect examples as follows:

Effect Example 1

Studies on the Solubility of Edaravone in Different vehicles

The selection of pharmaceutical vehicles is the most important step for the development of Liquid Oral formulation. In separate glass vials, 1 mL of each vehicles as shown in FIG. 1 was taken. An excess amount of Edaravone was added to the above mentioned solutions followed by continuous rotation using a mechanical shaker (Axyos Technologies, Brisbane, Australia) throughout the test for 24 hours at room temperature. After reaching equilibrium, each vial was centrifuged at 3000 rpm for 5 min, and excess insoluble Edaravone was discarded by filtration through 0.45 µm PVDF syringe filter. Subsequently, the filtrates were diluted using methanol. The solubility analysis was performed in triplicate by using the previously developed and validated HPLC method. The analysis of the samples was performed on an HPLC (Shimadzu, Kyoto, Japan) system equipped with a UV-VIS detector [SPD-20 A], DGU-20A3 online degasser, CBM-20A system controller, SIL-20AHT autosampler and a LC solution Chromopac data processor. Zorbax Eclipse XDB-C18 (4.6*150*3.5 mm$^3$) analytical column was used. Samples were analyzed with the mobile phase consisting of methanol, miliQ water and acetic acid at the ratio of 100:100:1 (v/v/v). The injection volume was 20 µL with a flow rate of 1 mL/min, and detection was performed at 240 nm.

To prepare Edaravone formulations, aqueous and non-aqueous solubilizers can be used alone or in combination in the present invention. The self-micro emulsified drug delivery system (SMEDDS, i.e., lipid based drug delivery system) is prepared by selecting ingredients (oils, surfactants and co-surfactants).

As can be seen from FIG. 1, Labrasol, Transcutol P, PEG 300, Caproyl PGMC and Cremophor RH 40 are preferable vehicles of Edaravone.

Effect Example 2

Screening Drug Carrier Soluplus
Screening Carriers

The selection of polymeric carrier is the most important step for the preparation of solid dispersions (SDs). To separate glass vials, 1%, 2%, 3%, 4%, 5% and 6% w/v solutions of different carriers was added, respectively. An excess amount of Edaravone was added to the above mentioned solutions followed by continuous rotation using a mechanical shaker (Axyos Technologies, Brisbane, Australia) throughout the test for 24 hours at room temperature. After reaching equilibrium, each vial was centrifuged at 3000 rpm for 5 min, and excess insoluble Edaravone was discarded by filtration through 0.45 µm PVDF syringe filter. Subsequently, the filtrates were diluted using methanol. The solubility analysis was performed in triplicate by using the previously developed and validated HPLC method.

Optimizing Solid Dispersion Based systems

The inventors prepared a number of batches of solid dispersions by using different ratios of drug to polymer (1:1, 1:3, 1:5, 1:7, 1:8, 1:10, 1:13, and 1:16) in order to optimize the ratio to achieve the maximum solubility. Solvent evaporation technique and Buchi Rotavap II instrument were used to prepare solid dispersions. Required amounts of drug and soluplus were dissolved in ethanol, then the mixture was dried at 55-60° C. under vacuum (500-600 mbar). The inventors compared the solubility of the optimized ratio with physical mixture of the same ratio (1:5) of drug to polymer. Physical mixtures of Edaravone and soluplus were prepared by mixing using mortar and pestle. The product was collected and stored in a desiccator before analysis. To separate glass vials, 1 mL of water was added. An excess amount of Edaravone was added to the above mentioned solutions followed by continuous rotation using a mechanical shaker (Axyos Technologies, Brisbane, Australia) throughout the test for 24 hours at room temperature. After reaching equilibrium, each vial was centrifuged at 3000 rpm for 5 min, and excess insoluble Edaravone was discarded by filtration through 0.45 μm PVDF syringe filter. Subsequently, the filtrates were diluted using methanol. The solubility analysis was performed in triplicate by using the previously developed and validated HPLC method.

Figure 2:
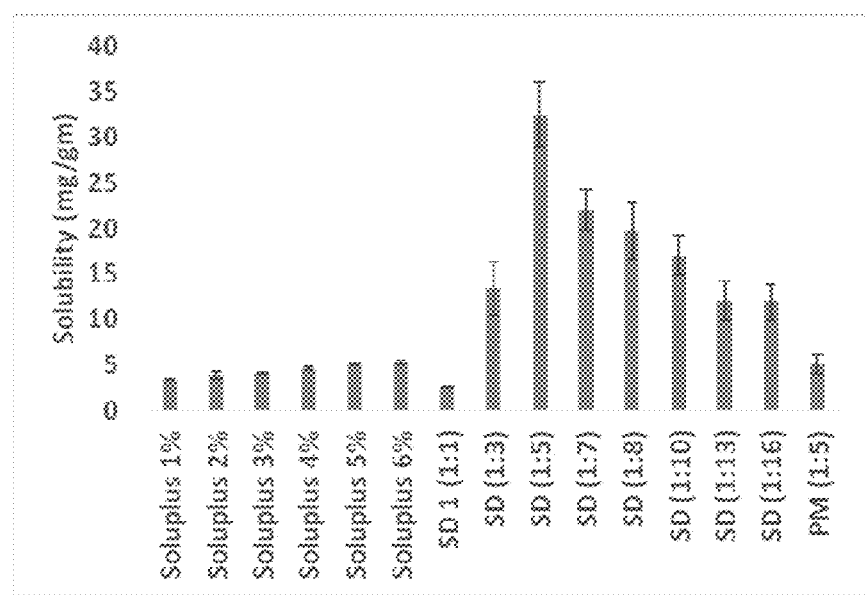
FIG. 2 shows the screening of a drug carrier system (Soluplus) based on the solubility study of Edaravone.

As can be seen from FIG. 2, it was demonstrated from studies that solubility improvement in concentration-dependent manner was found for soluplus. Later, the inventors optimized the ratio of drug to polymer. The optimized solid dispersion with a drug to soluplus ratio of 1:5 based system has capability to improve solubility significantly (18 folds) in water. The physical mixture (PM) of optimized drug to polymer ratio of 1:5 has an ability to enhance solubility more than 2 folds.

Effect Example 3

Solubility Studies of Edaravone in Different Solvents
Solubility Studies of Examples 1-5 and 9-11 Formulations To separate glass vials, 1 mL of each formulation was added. An excess amount of Edaravone was added to the above mentioned solutions followed by continuous rotation using a mechanical shaker (Axyos Technologies, Brisbane, Australia) throughout the test for 24 hours at room temperature. After reaching equilibrium, each vial was centrifuged at 3000 rpm for 5 min, and excess insoluble Edaravone was discarded by filtration through 0.45 μm PVDF syringe filter. Subsequently, the filtrates were diluted using methanol. The solubility analysis was performed in triplicate by using the previously developed and validated HPLC method.

Solubility Study of Example 6 Formulation

An excess quantity of Edaravone, and the required quantity of Soluplus and TPGS 1000 were dissolved in ethanol. The organic solvent was removed by Buchi Rotavap II instrument. The film formed was dried in vacuum desiccator overnight, hydrated with 10 mL 1× PBS buffer (pH 7.4), incubated at 37° C. for 30 min, and then sonicated for a few minutes. Each sample was centrifuged at 3000 rpm for 5 min. The resultant mixture was filtered through 0.45 μm syringe filter (PVDF). The solubility analysis was performed in triplicate by using the previously developed and validated HPLC method.

Solubility Studies of Examples 7 and 8 Formulations

To separate glass vials, 1 mL of water was added. An excess amount of solid dispersions was added to the above mentioned solutions followed by continuous rotation using a mechanical shaker (Axyos Technologies, Australia) throughout the test for 24 hours at room temperature. After reaching equilibrium, each vial was centrifuged at 3,000 rpm for 5 min, and excess insoluble Edaravone was discarded by filtration through 0.45 μm PVDF syringe filter. Subsequently, the filtrates were diluted using methanol. The solubility analysis was performed in triplicate by using the previously developed and validated HPLC method.

Figure 3:
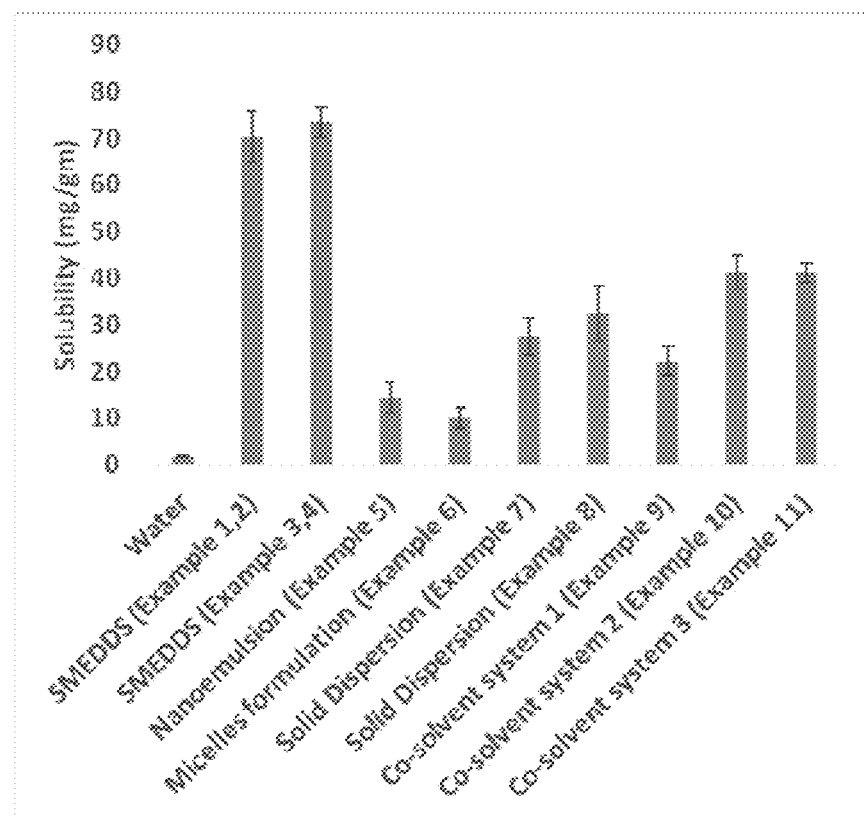
FIG. 3 shows the solubility of Edaravone in different types of formulations (Examples 1-11).

It was demonstrated that the solubility of Edaravone in all the formulations (Examples 1-11), especially SMEDDS of Examples 1-4, has a significant improvement than in water (FIG. 3).

Effect Example 4

Cell Toxicity Studies of SH-5Y5Y Cells
Cell Culture Assay

SH-SY5Y cell lines were used in order to perform cell culture. The DMEM media (Dulbecco's Modified Eagle Medium): Nutrient Mixture F12 in the ratio of 1:1 was used to culture cells respectively, supplemented with 10% FBS and 1% penicillin-streptomycin solution in 25 ml cell culture flask. Cells were cultivated in an incubator at 37° C. in presence of 5% $CO_2$.

MTT Assay on Cell Viability with SH-SY5Y

In the 96 well plate, SH-5YSY cells were seeded at the density of $5\times10^3$ cells/well. The culture media was changed after 24 hours with or without formulation-containing medium. The formulations were prepared by using previously sterilized water. A cell viability assay using MTT [3-(4,5-dimethylthiazol-2-yl)-2,5-diphenyltetrazolium bromide] methods was performed. After 20 h, 20 μL of MTT (Sigma-Aldrich, USA, 5 mg/ml in PBS), was added to each well and incubated for 1 h. 150 μL of DMSO was added to dissolve the insoluble purple formazan product to produce a colored solution. The optical density (OD) was read at 600 nm wavelength on the multi-well scanning spectrophotometer (BIO-RAD Model 2550 EIA Reader).

Figure 4:
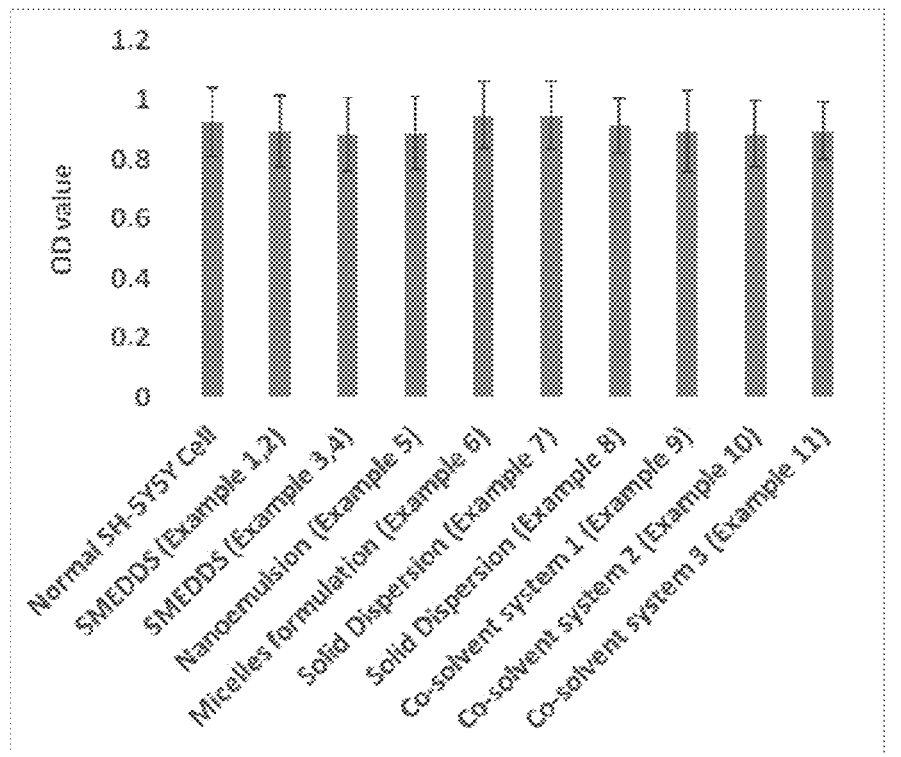
FIG. 4 shows the in vitro safety study of different types of Edaravone formulations (Examples 1-11).

As can be seen from FIG. 4, the in vitro safety of all formulations was confirmed as the inventors did not observe any significant toxicity from any of the formulations. The inventors found slight improvement of cell viability in cases of micelle formulation (Example 6) and solid dispersion (Example 7) because of the presence of TPGS 1000 which was reported as neuroprotection.

Effect Example 5

The Size Distribution of Edaravone Micellar Formulation

The size and size distribution of micellar formulation was measured by the dynamic light scattering (DLS) (Malvern Zeta Sizer Nano ZS). The samples were prepared by diluting the micellar solution with miliQ water and sonicated for 5 min before measurement. Particle size and Poly dispersity Index (PDI) were measured in triplicate by using protocol mentioned above.

Figure 5:
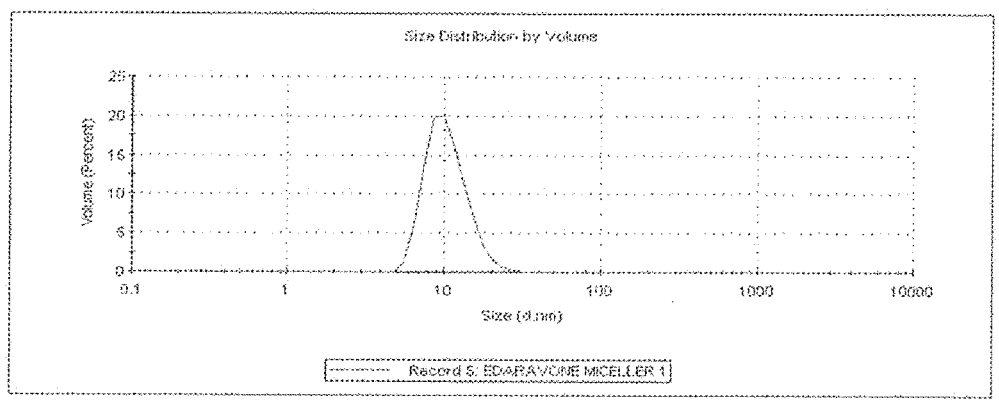
FIG. 5 shows the particle size distribution of micellar formulation (Example 6).

It is shown in FIG. 5 that because of the particle size in nano range, it has a potential to improve the cellular uptake of drug, resulting in an improvement of efficacy. This result also supports the results mentioned in FIG. 4 (Example 6).

Characteristic parameters of micellar formulation of the present invention (Example 6) were: particle size 15.68, polydispersity index 0.361, and drug loading 10.11 mg/ml.

Effect Example 6

Dissolution study of Edaravone in Solid Dispersion (SD)

The dissolution of SDs form was carried out by using USP type II paddle apparatus (AT 7 Smart, Sotax GmbH, Germany). The operating parameters were: 50 rpm rotation speed, 37±0.5° C. temperature, and SGF (simulated gastric fluid) 1.2 pH (USP), FaSSIF pH 5.0 (fasted state simulating Intestinal fluid), FeSSIF (fed state simulating Intestinal fluid) pH 6.5, and SIF (Simulating Intestinal fluid) 7.5 pH (USP). The formulation equivalent to 100 mg of Edaravone was filled into a size '2' hard gelatin capsule. Capsules were then placed inside the sinker and put into dissolution vessel. The samples were collected at different time intervals and replaced with equal amount of fresh dissolution media each time. The samples were filtered through 0.45 μm PVDF syringe filter and analyzed by the previously developed HPLC method.

Figure 6:
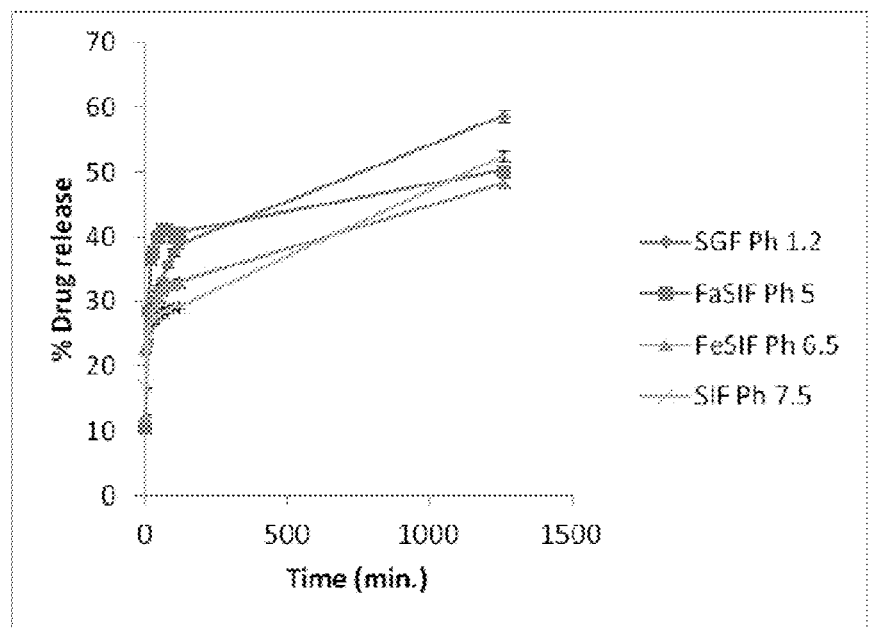
FIG. 6 shows the dissolution study of solid dispersion (Example 8) in different simulated body fluids.

As can be seen from FIG. 6, the solid dispersion of Example 8 can be used to prepare solid dosage form like a tablet or a capsule, and then the inventors have performed dissolution study to predict its behavior in various simulated biological fluids.

The inventors have found that the solid dispersion based formulation can provide sustained release after an initial burst release.

Effect Example 7

Bioavailability of Edaravone in SMEDDS Formulation

Male Sprague-Dawley rats (250±10 g) were acquired at least 1 week before starting the experiments as they were adapted to the laboratory environment, food, and water available for them. Rats were anaesthetized before operations. A longitudinal cut was made on the neck part and the area nearer to the jugular vein. Later, filled the catheter with 20 units/ml of heparin saline solution and inserted the catheter into the jugular vein up to first silicon stopper. The catheter was fixed over there by stitching the stopper and muscle. The other end of the catheter was passed beneath the skin of neck portion and nearer to ears. Lastly, filled the catheter with 500 unit/ml of heparin saline solution and plugged into the free end of catheter. After the surgery, the rats were kept in different cages for recovery. Then, on the next day, pharmacokinetic study of every rat would be carried out. Animals were fasted for 12 h before drug administration with free access to water.

Edaravone suspension was prepared by adding Edaravone into 0.5% carboxymethylcellulose sodium (CMC-Na) solution and then ultrasonicated for several minutes to obtain homogenous suspensions. Two groups of rats were orally administrated with Edaravone suspension, and SMEDDS at an equivalent dose of 30 mg/kg of Edaravone, respectively. One group of rats was administered through iv route. After administration of drug and formulation by oral gavage, 0.2 ml of blood samples were collected at time intervals of 0, 15, 30, 45, 60, 90, 120, 180, 240, 300, 360, 420, and 480 minutes. Each time, when blood samples were collected, catheter would be flushed with the same amount of heparin saline solution. After collection of blood samples, they were centrifuged at 5000 rpm for 5 min at 4° C. to separate plasma from blood. Plasma was separated and stored at −20° C. until analysis. Plasma (200 μl) was added with 40 μl of 30% $HClO_4$ to acidify plasma and precipitate the protein. After that, centrifuged at 4° C. and 16000 rpm for 6 minutes. The contents were diluted in methanol/water (50:50) and filtrated through 0.22 μm membrane filter before injected into LC/MS/MS.

The analysis of the samples was performed on Quadrapole LC/MS/MS (Shimadzu, Kyoto, Japan) system equipped with API 3000 mass spectrometer, Shimadzu SIL 20A autosampler, Shimadzu LC20AD Pump and an Analyst 1.6.2 data processor. Concentrations of the Edaravone in plasma were quantified using a newly developed and validated LC/MS/MS method. The extracts were reconstituted in methanol/water (50:50), injected into a Shimadzu Nexera HPLC system and resolved on a Kinetex C18 2.6 mm×50 mm×3 mm column (Phenomenex) with a mobile phase flow rate of 0.2 mL/min and an injection volume of 15 μL. Mobile phase A (MPA) was 5% methanol and 0.1% formic acid in water and mobile phase B (MPB) was 95% methanol and 0.1% formic acid in water. The mobile phase timetable was set as a gradient from 15% MPB initially to 70% MPB in 7.5 min, held to 100% MPB for further 0.5 min, then 15% MPB for 2 min in preparation for the next sample. The total run time for each sample analysis was 10 min. The column effluent was introduced into mass spectrometry using electro spray ionisation (ESI) in negative mode. The operating parameters of the ionisation source, including analyte-dependent parameters and source-dependent parameters were optimized to obtain the optimum performance of the mass spectrometer for the analysis. MRM analysis was conducted by monitoring the precursor ion to produce ion transitions (m/z) as follows: Edaravone 175.0/133.10 and Phenazone 189.1/147.1. Zero air was used as the source gas while nitrogen was used as both the curtain and collision gas. Peak areas were obtained from the compounds, and IS and known concentrations of calibrators were used to construct a calibration curve from compounds/IS area ratios. The limit of quantification was 5 ng/mL. The intraday and interday variability for each compound was within 15%.

Figure 7:
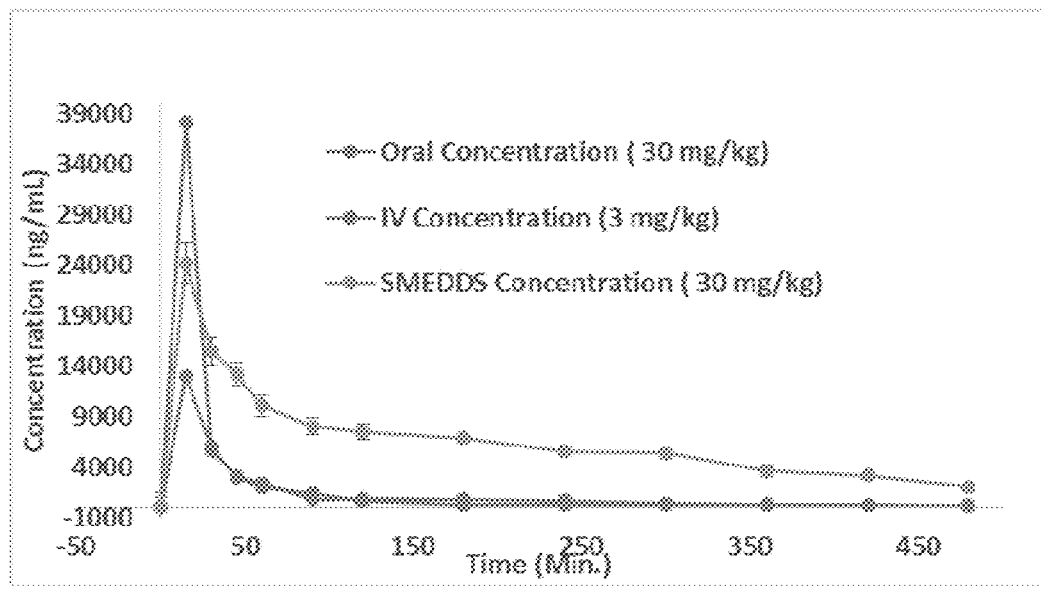
FIG. 7 shows the bioavailability study of SMEDDS (Examples 1 and 2).

To study the bioavailability of self-microemulsifying drug delivery system (SMEDDS) of the present invention (Examples 1 and 2), Edaravone was orally administered in suspension form (prepared by adding Edaravone into 0.5 carboxymethylcellulose sodium (CMC-Na) solution), and Edaravone via iv route was used as a control. The bioavailability of SMEDDS was significantly improved compared to Edaravone suspension (FIG. 7). SMEDDS can also improve the half-life of the drug which shows a potential to maintain therapeutic level at a longer time.

Effect Example 8

Stability Studies of Edaravone in Solid Dispersion

Simulated gastrointestinal fluids (without enzymes and bile component) were prepared according to the USP methods. SGF (simulated gastric fluid) 1.2 pH (USP) and SIF (Simulating Intestinal fluid) 6.8 pH (USP) and 7.4 pH. To determine the chemical stability of SD formulations, the solutions in miliQ water was prepared and used. SD formulation was dissolved in aforesaid buffer solutions. Samples were collected at the predetermined time interval and filtered through 0.45 μm PVDF syringe filter. All samples were analysed in triplicate by HPLC.

Figure 8A:
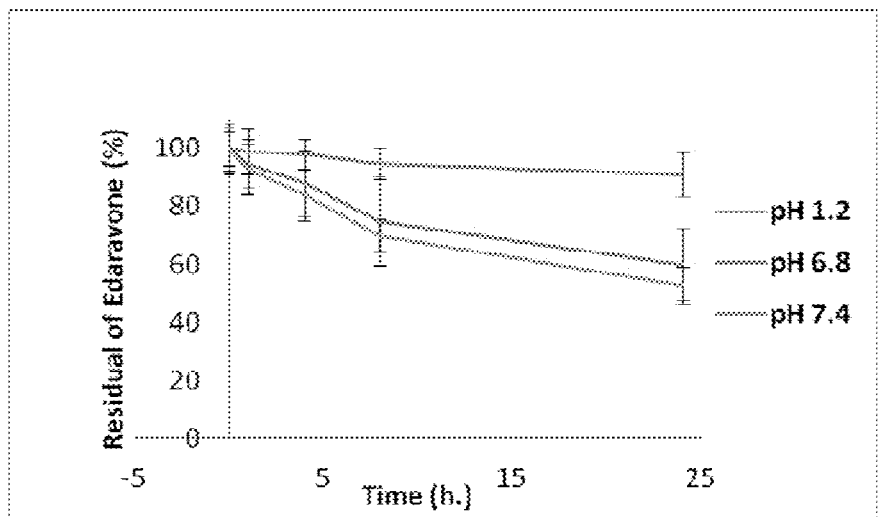
FIG. 8A shows the stability study of Edaravone in biorelevant media at various pHs.

It was demonstrated in FIG. 8A that Edaravone showed significant degradation at neutral to basic pH, but it maintained substantially constant at acidic pH.

Figure 8B:
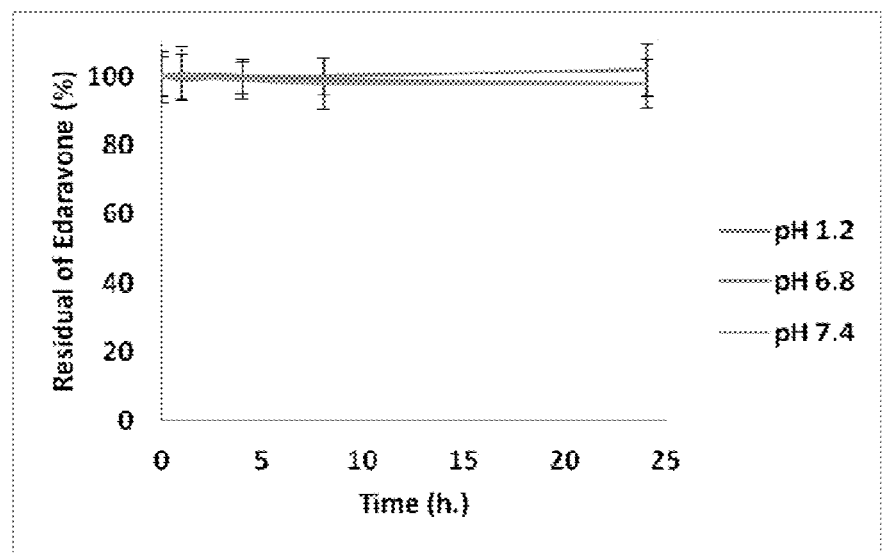
FIG. 8B shows the stability study of the solid dispersion (Example 8) in biorelevant media at various pHs.

It was demonstrated in FIG. 8B that the solid dispersion of the present invention (Example 8) can protect Edaravone from degradation in various biorelevant media.

The above examples are merely to help understand the core spirits of the present invention. It should be noted that, for those skilled in the art, several improvements or modifications can be made to the novel formulations and preparation methods of the present invention, without departing from the principle of the present invention, which, however, fall into the scopes of the appended claims.

REFERENCES

1. Bernabeu, E., et al., Novel Soluplus®-TPGS mixed micelles for encapsulation of paclitaxel with enhanced in vitro cytotoxicity on breast and ovarian cancer cell lines. Colloids Surf B Biointerfaces, 2016. 140: p. 403-11.
2. Dian, L., et al., Enhancing oral bioavailability of quercetin using novel soluplus polymeric micelles. Nanoscale Res Lett, 2014. 9(1): p. 2406.
3. Jin, X., et al., Soluplus® micelles as a potential drug delivery system for reversal of resistant tumor. Biomed Pharmacother, 2015. 69: p. 388-95.
4. Xia, D., et al., Supersaturated polymeric micelles for oral cyclosporine A delivery: The role of Soluplus-sodium dodecyl sulfate complex. Colloids Surf B Biointerfaces, 2016. 141: p. 301-310.
5. Strickley, R. G., Solubilizing excipients in oral and injectable formulations. Pharm Res, 2004. 21(2): p. 201-30.

What is claimed is:

1. A solid phase dispersion formulation, comprising Edaravone as an active ingredient, and a polymer carrier selected from Soluplus, wherein the solid phase dispersion comprises Edaravone and Soluplus in a ratio of Edaravone:Soluplus of 1:1 to 1:16 by mass.

2. The solid phase dispersion formulation of claim 1, further comprising a surfactant.

3. The solid phase dispersion formulation of claim 2, wherein the surfactant includes an anionic, cationic, or amphoteric surfactant, selected from the group consisting of sodium dodecanesulfonate, sodium dodecyl sulfate (SDS), sodium lauryl sulfate (SLS), polyoxyethylene sorbitan long-chain fatty acid esters, Vitamin E-TPGS, bile salts, sodium deoxycholate, sodium glycocholate, polyoxyethylene poly-oxypropylene glycols and combinations thereof.

4. The solid phase dispersion formulation of claim 2, wherein the surfactant is TPGS 1000.

5. The solid phase dispersion formulation of claim 1, comprising Edaravone, Soluplus and optionally TPGS 1000.

6. A method of preparing the solid phase dispersion formulation of claim 1, comprising a step of:
dispersing Edaravone or a pharmaceutically acceptable salt thereof as an active ingredient in a polymer carrier and, optionally, a surfactant.

7. The method of claim 6, further comprising a step selected from: melting ice bath agitation, thin film cooling, liquid nitrogen, spray congealing, hot-melt extrusion, Melt-rex™, melt agglomeration or solvent evaporation, including oven drying, vacuum drying, rotary evaporation, heating on hot plate, spray drying, freeze drying, supercritical anti-solvent, co-precipitation, electrostatic spinning, spray freeze drying, ultra-rapid freezing or fluid-bed coating, and solvent melting.

8. The solid phase dispersion formulation of claim 1, comprising Edaravone and Soluplus in a ratio of Edaravone:Soluplus of 1:5 by mass.

9. An oral pharmaceutical composition comprising Edaravone or a pharmaceutically acceptable salt thereof, and Soluplus in a ratio of Edaravone:Soluplus of 1:1 to 1:16 by mass.

* * * * *